(12) United States Patent
Koshigaya et al.

(10) Patent No.: US 12,415,006 B2
(45) Date of Patent: Sep. 16, 2025

(54) INFORMATION PROCESSING APPARATUS AND METHOD OF CONTROLLING INFORMATION PROCESSING APPARATUS

(71) Applicant: CANON KABUSHIKI KAISHA, Tokyo (JP)

(72) Inventors: Motoki Koshigaya, Saitama (JP); Tsutomu Kubota, Chiba (JP); Tatsuya Ogawa, Ibaraki (JP); Hidetaka Tabuchi, Chiba (JP); Tsunahito Nakashita, Chiba (JP)

(73) Assignee: Canon Kabushiki Kaisha, Tokyo (JP)

( * ) Notice: Subject to any disclaimer, the term of this patent is extended or adjusted under 35 U.S.C. 154(b) by 678 days.

(21) Appl. No.: 17/743,259

(22) Filed: May 12, 2022

(65) Prior Publication Data
US 2022/0362418 A1 Nov. 17, 2022

(30) Foreign Application Priority Data
May 14, 2021 (JP) .................. 2021-082585

(51) Int. Cl.
*A61L 2/10* (2006.01)
*A61L 2/24* (2006.01)

(52) U.S. Cl.
CPC .................. *A61L 2/10* (2013.01); *A61L 2/24* (2013.01); *A61L 2202/14* (2013.01)

(58) Field of Classification Search
CPC ........... A61L 2/10; A61L 2/24; A61L 2202/14
See application file for complete search history.

(56) References Cited

U.S. PATENT DOCUMENTS

2020/0197550 A1* 6/2020 Barron .................. F21V 29/503
2021/0052757 A1* 2/2021 Baarman ................ G16H 10/60

FOREIGN PATENT DOCUMENTS

| CN | 108765205 A | * | 11/2018 |
| CN | 112733358 A | * | 4/2021 |
| JP | 2006204824 A | | 8/2006 |
| JP | 2014110496 A | * | 6/2014 |

\* cited by examiner

*Primary Examiner* — Donald R Spamer
*Assistant Examiner* — Kayla Rose Sarantakos
(74) *Attorney, Agent, or Firm* — Canon U.S.A., Inc. IP Division

(57) ABSTRACT

An information processing apparatus includes a sterilization unit that performs sterilization with an ultraviolet light source a part of the information processing apparatus that is operated on, a management unit that manages lifetime information corresponding to a product lifetime of the ultraviolet light source and usage information corresponding to an irradiation time and an irradiation output of the ultraviolet light source, and a control unit that controls the ultraviolet light source in a first control mode of controlling the ultraviolet light source with a first irradiation time and a first irradiation output or in a second control mode of controlling the ultraviolet light source with a second irradiation time shorter than the first irradiation time and a second irradiation output higher than the first irradiation output.

13 Claims, 11 Drawing Sheets

FIG.6A

| | |
|---|---|
| 601 — LIFETIME END POINT | 108,000,000 |
| 602 — LIFETIME WARNING POINT | 102,600,000 |
| 603 — LIFETIME CAUTION POINT | 97,200,000 |
| 604 — REFERENCE LIGHT QUANTITY SETTING LIFETIME DETERIORATION RATE α | 1 |
| 605 — LOW OUTPUT LIGHT QUANTITY SETTING LIFETIME DETERIORATION RATE β | 2 |
| 606 — HIGH OUTPUT LIGHT QUANTITY SETTING LIFETIME DETERIORATION RATE γ | 4 |
| 607 — REFERENCE LIGHT QUANTITY SETTING STERILIZATION TIME [SEC] | 16 |
| 608 — LOW OUTPUT LIGHT QUANTITY SETTING STERILIZATION TIME [SEC] | 8 |
| 609 — HIGH OUTPUT LIGHT QUANTITY SETTING STERILIZATION TIME [SEC] | 4 |

FIG.6B

| | 621 — ULTRAVIOLET LIGHT SOURCE 200a (NEAR OPERATION UNIT 12) | 622 — ULTRAVIOLET LIGHT SOURCE 200b (NEAR SCANNER UNIT 13) | 623 — ULTRAVIOLET LIGHT SOURCE 200c (NEAR POWER SWITCH 250) | 624 — ULTRAVIOLET LIGHT SOURCE 200d (NEAR SHEET FEEDING CASSETTE 15) |
|---|---|---|---|---|
| 611 — ULTRAVIOLET LIGHT SOURCE 200 LOW OUTPUT INTEGRATED TIME [SEC] | 0 | 48,540,000 | 11,680 | 86,720 |
| 612 — ULTRAVIOLET LIGHT SOURCE 200 HIGH OUTPUT INTEGRATED TIME [SEC] | 25,650,000 | 30,100 | 0 | 0 |
| 613 — ULTRAVIOLET LIGHT SOURCE 200 DETERIORATION INTEGRATED POINT [SEC] | 102,600,000 | 97,200,300 | 22,360 | 173,440 |

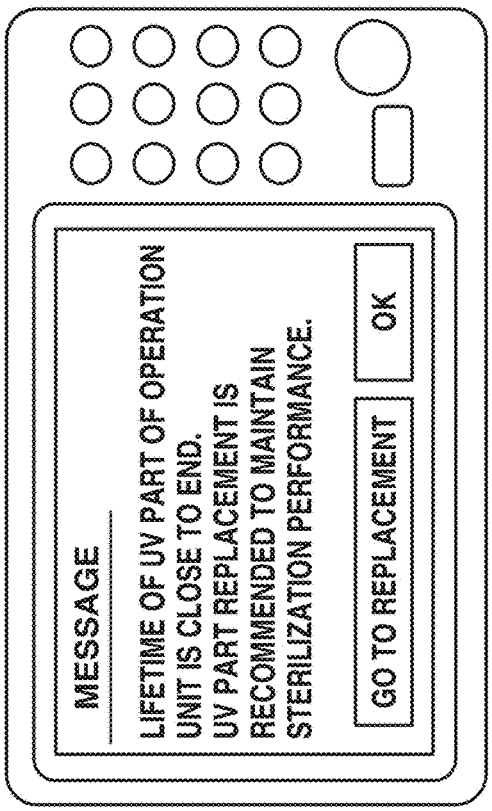
FIG.7A
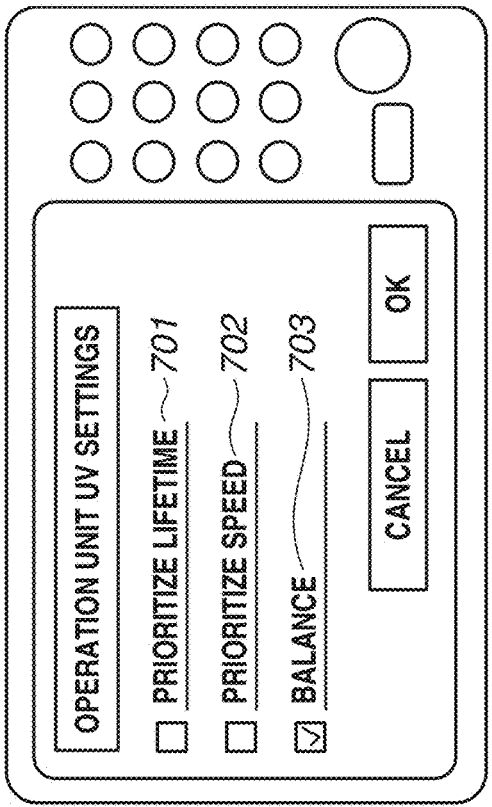
FIG.7C
FIG.7B
FIG.7D

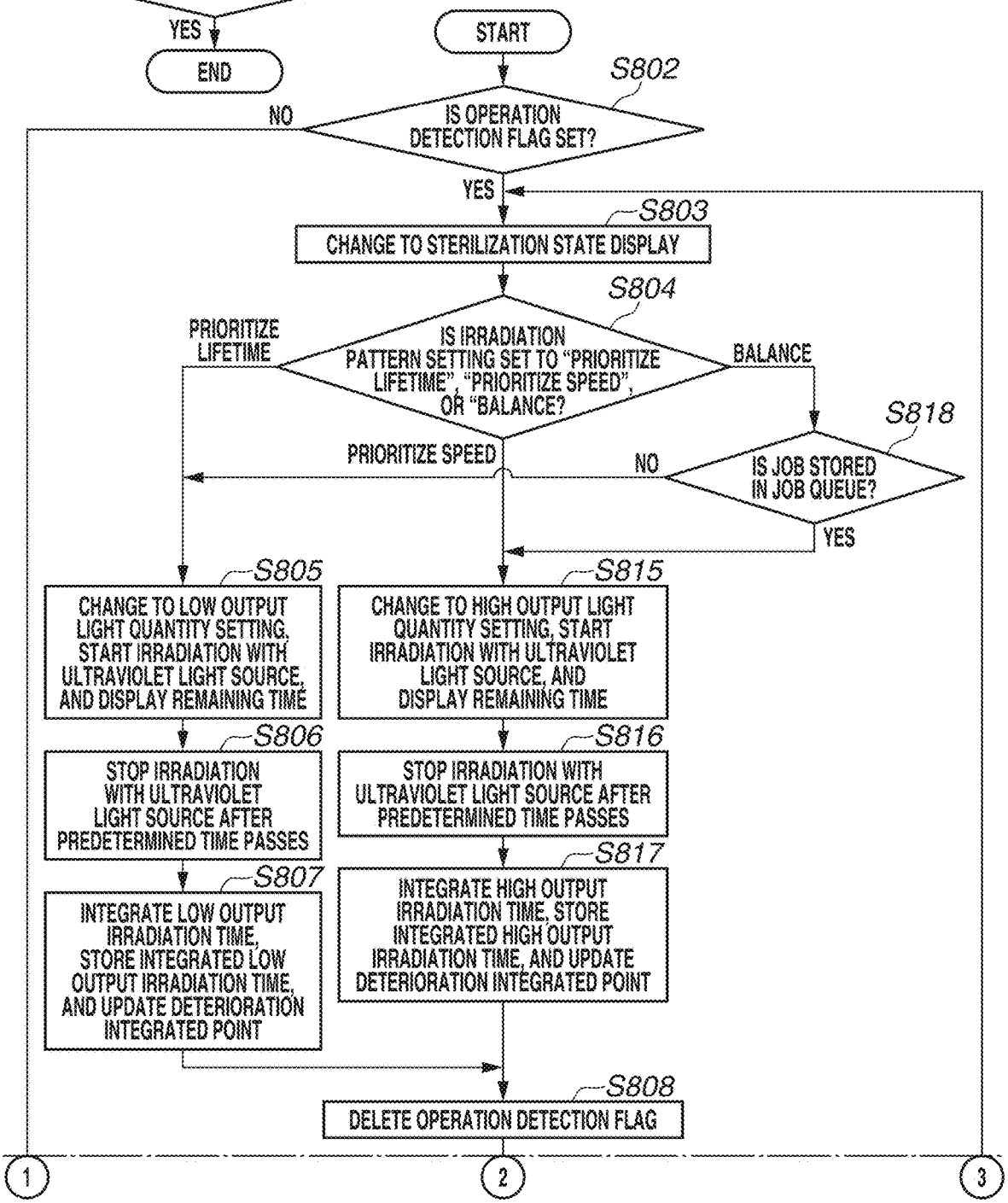

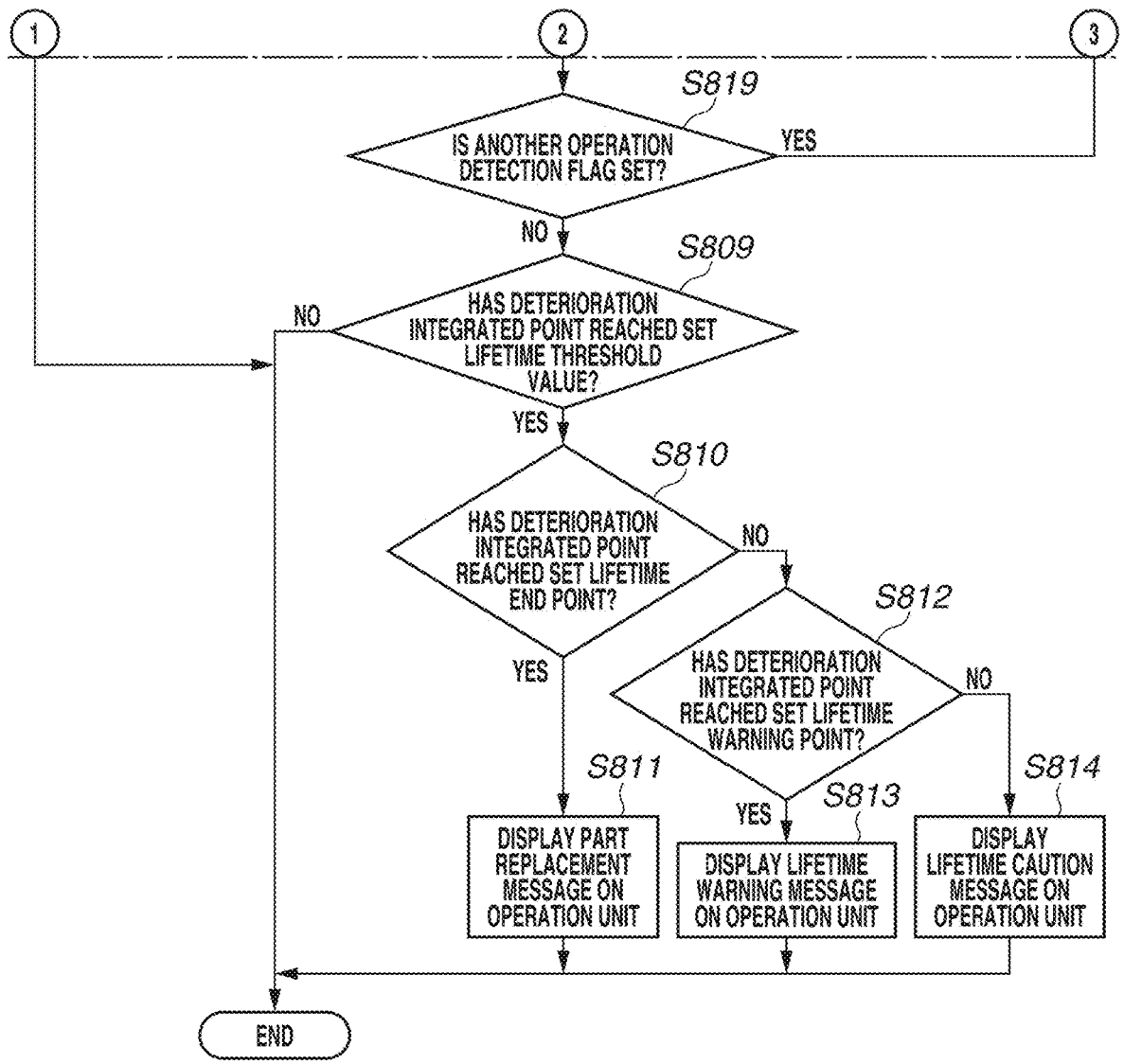

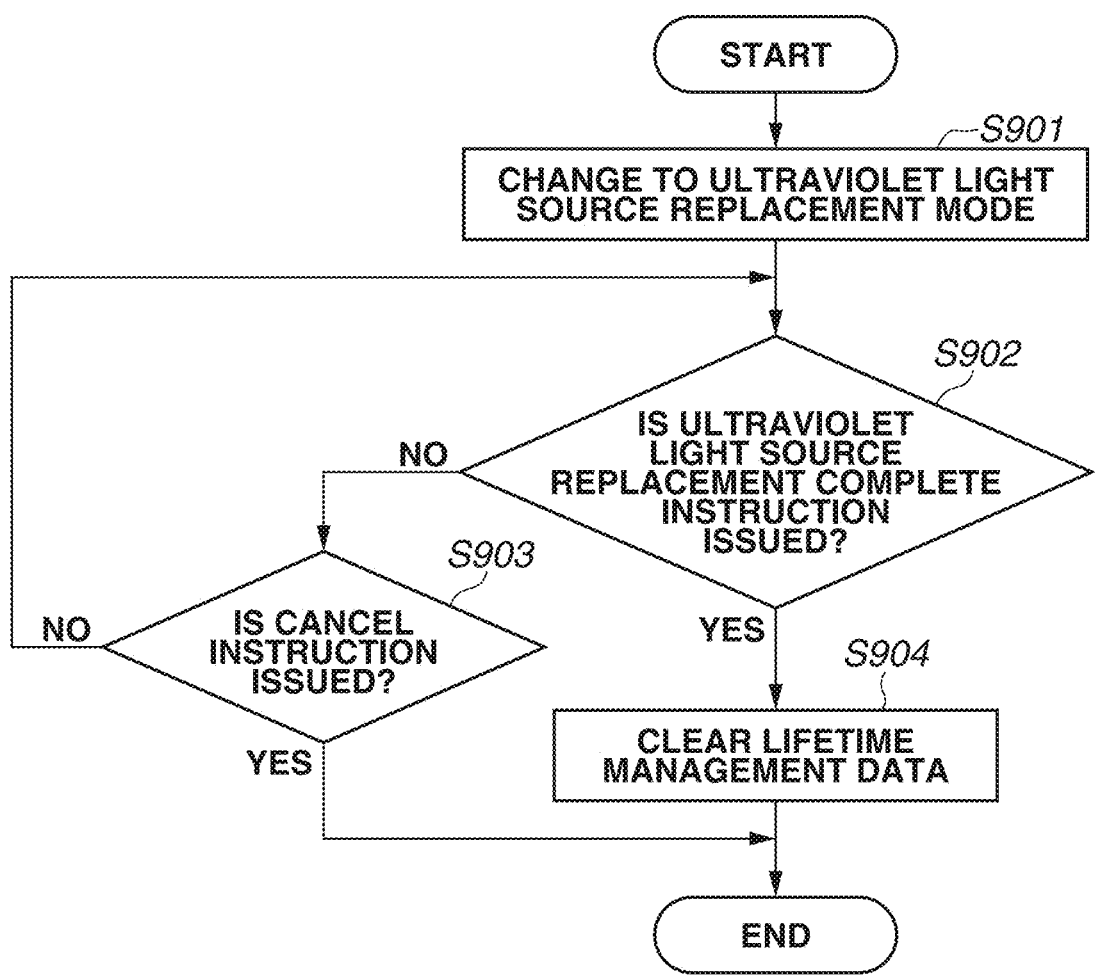

INFORMATION PROCESSING APPARATUS AND METHOD OF CONTROLLING INFORMATION PROCESSING APPARATUS

BACKGROUND

Field

The present disclosure relates to an information processing apparatus with a sterilization function using an ultraviolet light source.

Description of the Related Art

Image forming apparatuses such as copy machines or multi-function peripherals are generally available to the public. As a result of being used by one user after another, where each user can touch various locations on the multi-function peripherals, as well airborne droplets from each user possibly landing on the multi-peripherals, portions of or the entire apparatus can become contaminated with microorganisms such as viruses. Research results indicate that viruses can remain infectious for many days on hard surfaces, such as glass or plastic surfaces.

As a result, viruses can cause infection spread via touches on contaminated apparatuses. In particular, the coronavirus, or COVID-19 that has spread since the beginning of 2020 is highly infectious, and sterilization of facilities and articles for public use has become necessary. A commonly-used sterilization method is the use of ethanol disinfectant, but this method can be unsuitable for some portions of an electronic device, such as an image forming apparatus.

Methods of sterilization by ultraviolet irradiation are becoming more common. For example, Japanese Patent Application Laid-Open No. 2006-204824 discusses a sterilization method in which the front or rear surface of an operation panel of an operation unit frequently used by users is irradiated with a sterilization lamp after a user uses the operation panel. Ultraviolet light source devices for sterilization with wavelengths of especially 200 nm to 290 nm have become available.

There are various types of ultraviolet light source devices. Examples ultraviolet light source devices for sterilization include mercury lamps, excimer lamps, and light emitting diodes (LEDs), where each has its own advantages and disadvantages. Mercury lamps are high in output but are unsuitable for use in image forming apparatuses because a mercury lamp cannot shine or blink due to its long activation time. Excimer lamps and LEDs are suitable for use in image forming apparatuses because they can instantly shine and blink. While excimer lamps are high in output, unlike LEDs, excimer lamps cannot be reduced in size, which results in a limited degree of freedom. LEDs are small in size, have long lifetime, and are low in power consumption. LEDs with wavelengths of 265 nm and 275 nm are currently available on the market, but have a disadvantage that the irradiation output decreases at shorter wavelengths.

Important factors in sterilization using an ultraviolet light source include the quantity of light from the light source and the distance, the angle, and the irradiation time from the light source to the sterilization target. In other words, a target can be insufficiently sterilized unless these four conditions (quantity of light, distance, angle, and time of irradiation) are satisfied and an integrated illuminance sufficient for sterilization is applied. The integrated illuminance is the product of an illuminance and the number of seconds and is in the unit of joules/cm$^2$ (J/cm$^2$). The illuminance represents the intensity of light. The illuminance is inversely proportional to the square of the distance to a target object with respect to the light source output and is proportional to the cosine of an angle of incidence θ. For example, an experiment result of inactivating noroviruses indicates that irradiation with an ultraviolet light emitting diode (ultraviolet LED) having a light output of 7 mW at a distance of 10 cm for 30 minutes resulted in a decrease to a detection limit or lower. Thus, in order to mount an ultraviolet light source on an image forming apparatus and perform sterilization in a short time (several seconds), the ultraviolet light source is set to a high output and irradiates a target object from the shortest possible distance.

The method discussed in Japanese Patent Application Laid-Open No. 2006-204824 only mentions that the light from a sterilization lamp is projected directly on a target object, and it does not satisfy the factors for sterilization. In sterilization using ultraviolet rays, it is insufficient to simply project ultraviolet rays on a target object since the quantity of light and the time of irradiation are important as described above. For an image forming apparatus provided with ultraviolet light sources to irradiate each portion that is likely to be touched by users, the time of sterilization is determined depending on the irradiation target portion and output and the location of the light source, but the sterilization does not end instantly and takes several seconds to several minutes.

The lifetime of an ultraviolet light source device depends significantly on how light is emitted. For example, the light output of excimer lamps and that of LEDs are decreased by 70% after about 3,000-hour irradiation and 30,000-hour irradiation, respectively, in the reference light quantity setting, which can vary depending on manufacturers.

A doubled output of the light quantity to reduce the irradiation time causes a doubled deterioration rate. For example, the continuation of that setting will halve the lifetime of LEDs to 15,000 hours. Thus, that prevents a simple control of sterilization with a high output of irradiation for a short time for convenience for users.

Thus, there have been demands for ensuring both the lifetime of an ultraviolet light source device and user convenience.

SUMMARY

According to an aspect of the present disclosure, an information processing apparatus includes a sterilization unit configured to perform sterilization with an ultraviolet light source on a part of the information processing apparatus that is operated on, a management unit configured to manage lifetime information corresponding to a product lifetime of the ultraviolet light source and usage information corresponding to an irradiation time and an irradiation output of the ultraviolet light source, and a control unit configured to control the ultraviolet light source in a first control mode of controlling the ultraviolet light source with a first irradiation time and a first irradiation output or in a second control mode of controlling the ultraviolet light source with a second irradiation time shorter than the first irradiation time and a second irradiation output higher than the first irradiation output.

Further features will become apparent from the following description of exemplary embodiments with reference to the attached drawings.

BRIEF DESCRIPTION OF THE DRAWINGS

FIGS. 6A and 6B illustrate an example of setting values and management data that relate to the ultraviolet light sources.

FIGS. 7A to 7G illustrate an example of a display screen of the operation unit.

FIGS. 8A and 8B1 and 8B2 are flowcharts illustrating a process of adjusting the light quantity of an ultraviolet light source and managing a lifetime.

FIG. 9 is a flowchart illustrating a process of replacing an ultraviolet light source and clearing management data.

DESCRIPTION OF THE EMBODIMENTS

Exemplary embodiments will be described in detail below with reference to the attached drawings. The below-described exemplary embodiments are not intended to limit the scope of the claims and not all combinations of features described in the exemplary embodiments are always used in a technical solution of the present disclosure. While an image processing apparatus is described below as an example of an information processing apparatus according to an exemplary embodiment(s), the description is not seen to be limiting.

Figure 1:
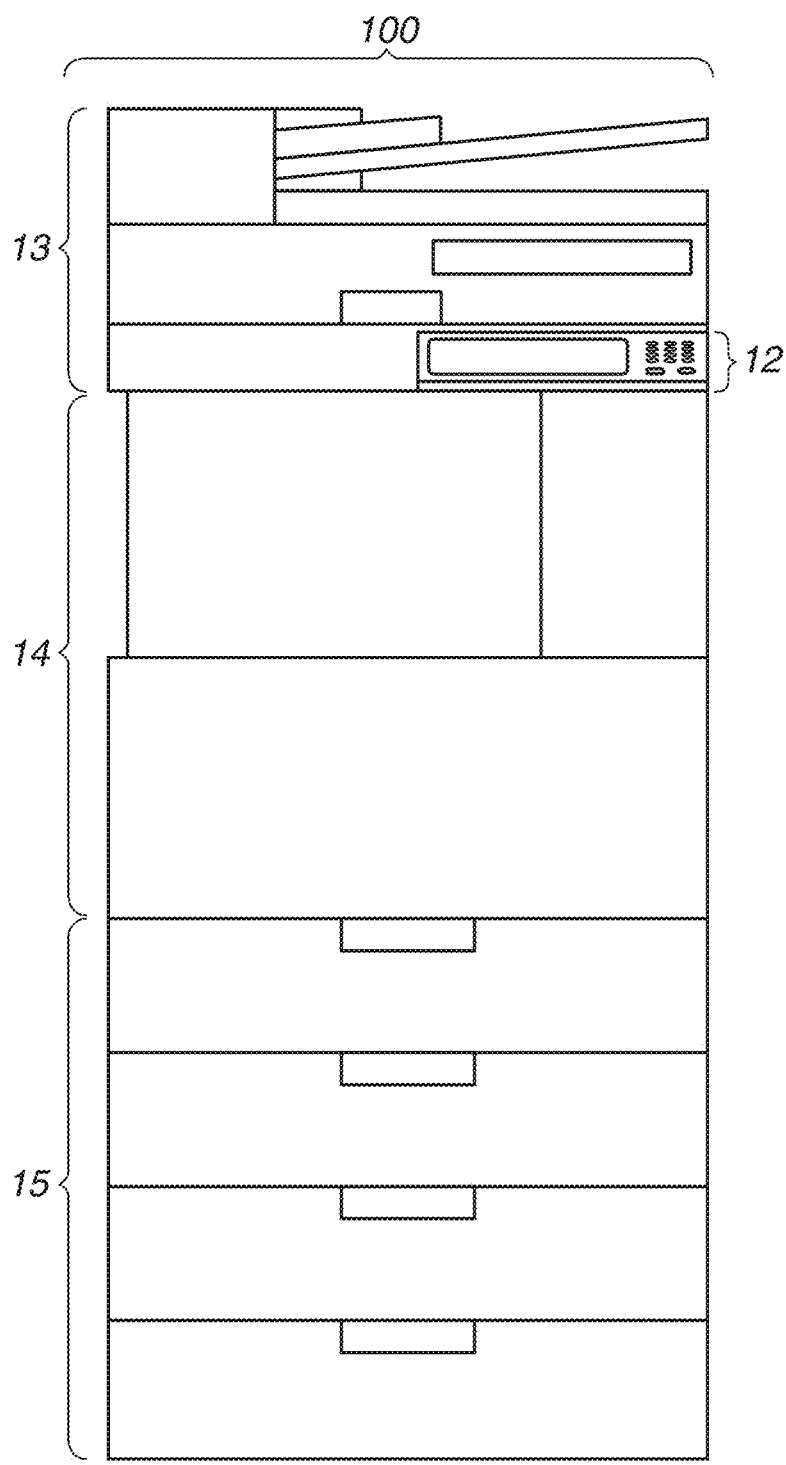
FIG. 1 is a front external view illustrating an image forming apparatus.

FIG. 1 is an external view illustrating an image forming apparatus 100 according to an exemplary embodiment. The image forming apparatus 100 is a multi-function peripheral (MFP) with a plurality of functions such as a print function, a scanner function, a copy function, and a facsimile function. Details of the components will be described below with reference to the drawings.

Figure 2:
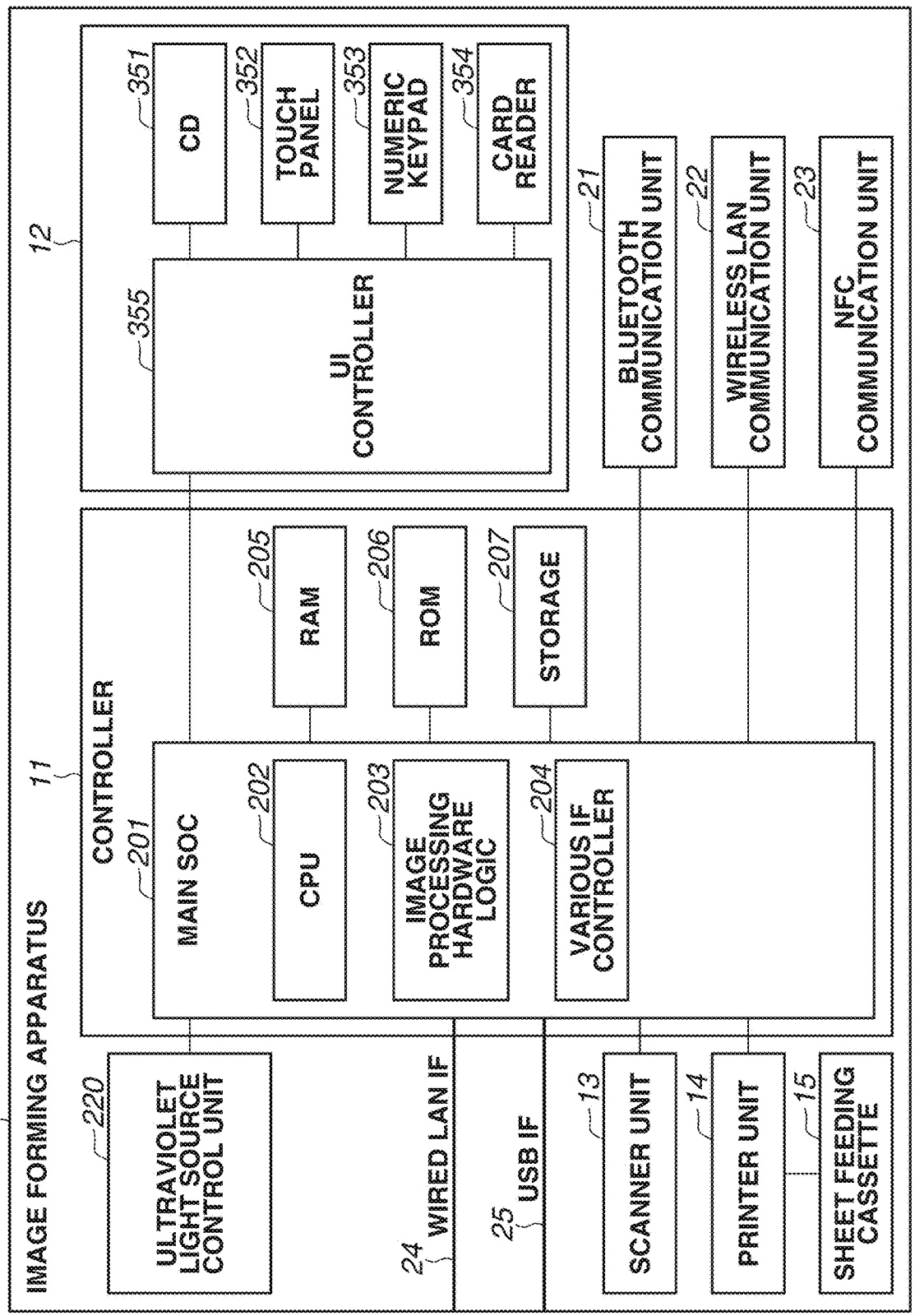
FIG. 2 is a hardware block diagram illustrating the image forming apparatus.

FIG. 2 is a block diagram illustrating an internal hardware configuration of the image forming apparatus 100 illustrated in FIG. 1. Details of a controller 11 configured to control general operations of the image forming apparatus 100 will be described below. As illustrated in FIG. 1, the image forming apparatus 100 includes functional units such as the controller 11, an operation unit 12, a scanner unit 13, a printer unit 14, and sheet feeding cassettes 15. The controller 11 controls operations of the image forming apparatus 100. The above-described units cooperate with one another to carry out the functions such as the print function, the scan function, and the copy function.

The controller 11 includes a main system-on-a-chip (main SOC) 201. The main SOC 201 is an integrated circuit part and includes a central processing unit (CPU) 202, an image processing hardware logic 203, and various interfaces (various IF) controller 204. The CPU 202 in the controller 11 is a central processing unit that generally controls the image forming apparatus 100 and is connected to the functional units to comprehensively control various types of processing of the image forming apparatus 100.

The image processing hardware logic 203 performs image processing such as correction, processing, and editing on image data received from the scanner unit 13 or a wired local area network interface (wired LAN IF) 24. The image processing hardware logic 203 also performs processing such as color conversion, filter processing, and resolution conversion on image data to be output to the printer unit 14.

The various IF controller 204 is an interface controller such as a universal serial bus (USB) device, a serial advanced technology attachment (SATA), a random access memory (RAM), or a low voltage differential signaling (LVDS) device and connects to a Bluetooth® communication unit 21, a RAM 205 described below, a read-only memory (ROM) 206, and a storage 207. Details of the interfaces are not illustrated as they have no direct connection to the present disclosure. The main SOC 201 includes a system bus for connecting the Bluetooth® communication unit 21, the RAM 205, the ROM 206, and the storage 207. The RAM 205 is a system work memory that the CPU 202 uses to operate, and calculation data for and from the CPU 202 and various programs are stored in the RAM 205.

The RAM 205 is also used as an image memory for storing image data on which various types of image processing are performed by the image processing hardware logic 203 during scanning and printing. The ROM 206 is a boot ROM and stores a boot program for the controller 11.

The storage 207 is a non-volatile secondary storage device for storing large-size programs and large-size data, and the stored programs and data are loaded to the RAM 205 and used. The storage 207 can be, for example, a hard disk drive (HDD) or a solid state drive (SSD) standard memory device or can be an area section of the ROM 206. The operation unit 12 includes a user interface (UI) controller 355. The UI controller 355 controls a liquid crystal display (LCD) 351, a touch panel 352, a numeric keypad 353, and a card reader 354 in cooperation with the main SOC 201.

Figure 3:
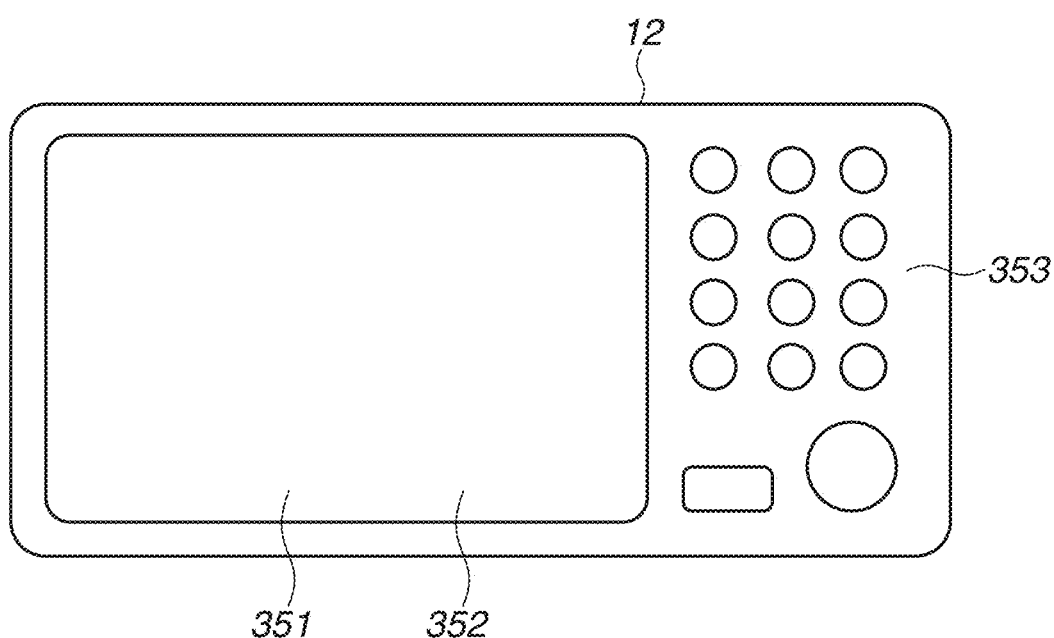
FIG. 3 is an external view illustrating an operation unit.

An exterior example of the operation unit 12 is illustrated in FIG. 3. User operations received via the touch panel 352 and the numeric keypad 353 are converted into data by the UI controller 355, and the UI controller 355 transmits the data to the main SOC 201. Screens are changed based on the transmitted data, and content displayed on the LCD 351 is changed based on the operation status on the image forming apparatus 100. If a user performs an identification (ID) reading operation on the card reader 354, the UI controller 355 receives the ID and transmits the ID to the main SOC 201 via the read ID information. Authentication processing is performed using authentication data stored in a main body (e.g., the storage 207) and a database, such as authentication data (accessed from the wired LAN IF 24) on a network.

A user can carry out functions of the image forming apparatus 100 by operating the operation unit 12. The scanner unit 13 is a unit that reads images and characters on sheets using a charge coupled device (CCD) sensor or a contact image sensor (CIS) and converts the read images and characters into image data. The printer unit 14 is a printer engine that prints image data on sheets and includes a laser scanner unit, a photosensitive drum, a sheet conveyance unit, and the sheet feeding cassette 15. The Bluetooth® communication unit 21 is an antenna module unit that includes a Bluetooth® controller.

A wireless local area network (wireless LAN) communication unit 22 is an antenna module unit that includes a wireless LAN controller. A near-field communication (NFC) communication unit 23 is an antenna module unit that includes a NFC controller. The wired LAN IF 24 is an interface for performing network communication via a LAN connector. A USB interface (USB IF) 25 is an interface for connecting to a personal computer to transmit and receive data via USB communication. An ultraviolet light source control unit 220 is a functional unit that controls ultraviolet irradiation to sterilize virus-contaminated parts according to the present exemplary embodiment. A detailed configuration of the ultraviolet light source control unit 220 will be described below with reference to FIG. 4. The hardware of the image forming apparatus 100 is configured as described above.

Figure 4:
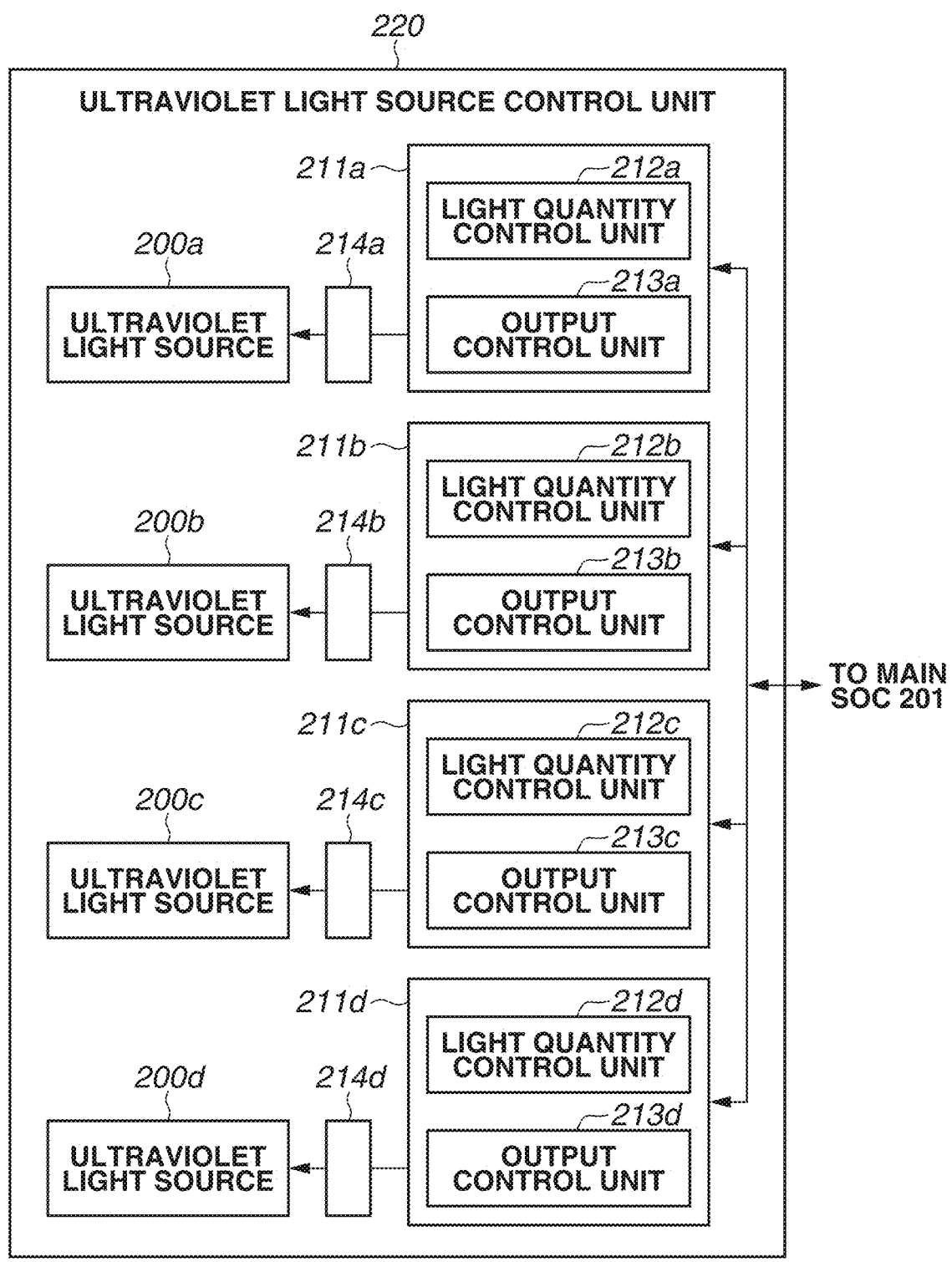
FIG. 4 is a block diagram illustrating an ultraviolet light source control unit.

FIG. 4 is a detailed block diagram illustrating the ultraviolet light source control unit 220 according to the present exemplary embodiment. The ultraviolet light source control unit 220 includes a control interface (control IN) unit 210 and a plurality of ultraviolet (UV) light control units 211 and is controlled by the main SOC 201 based on operation states of switches, the operation unit 12, the scanner unit 13, and the printer unit 14 (the sheet feeding cassette 15). Each UV light control unit 211 includes the corresponding light quantity control unit 212 and the corresponding output control unit 213. Each light quantity control unit 212 is a functional unit that controls the irradiation output of the connected ultraviolet light source 200, and the main SOC 201 sets an irradiation output setting.

Each ultraviolet light source 200 is a replaceable part connected to the corresponding removable connector 214. When the product lifetime of each ultraviolet light source 200 is insufficient to guarantee sterilization performance, a screen notification is displayed on the LCD 351 of the operation unit 12. This prompts the user or a serviceperson to replace the corresponding ultraviolet light source 200. Each output control unit 213 performs ON/OFF control on the connected ultraviolet light source 200 to perform irradiation at the irradiation output set by the corresponding light quantity control unit 212 based on an instruction from the main SOC 201.

In response to an input to the touch panel 352 or the numeric keypad 353 of the operation unit 12, the main SOC 201 determines that the operation unit 12 is touched by the user. Then, the instruction is transmitted to an UV light control unit 211a, and an ultraviolet light source 200a is turned on to perform irradiation at a set light quantity. After a predetermined irradiation time passes, the main SOC 201 transmits an OFF instruction to turn off the ultraviolet light source 200a. Operations on the scanner unit 13 cause the ON/OFF control to be similarly performed on an ultraviolet light source 200b. Operations on a power switch 250 cause the ON/OFF control to be similarly performed on an ultraviolet light source 200c. Operations on the printer unit 14 cause the ON/OFF control to be similarly performed on an ultraviolet light source 200d. In replacing an ultraviolet light source 200 due to the product lifetime, the main SOC 201 controls the corresponding output control unit 213 to change a circuit state to enable physical connector separation to prevent irradiation during the replacement.

Figure 5:
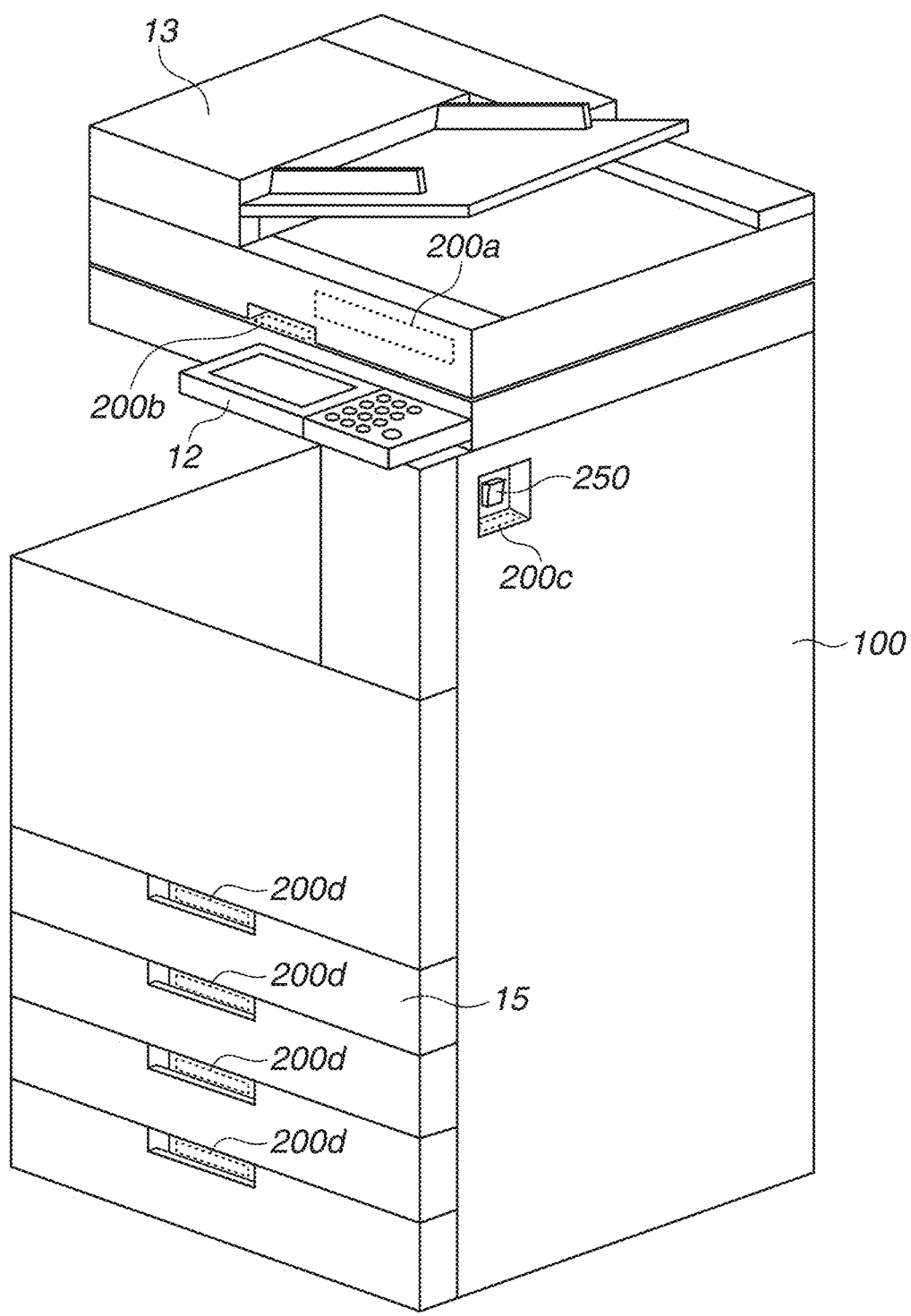
FIG. 5 is a perspective view illustrating an image forming apparatus 100 to show positions of ultraviolet light sources.

FIG. 5 is a perspective view illustrating positions of the ultraviolet light sources 200 on the image forming apparatus 100 according to the present exemplary embodiment. FIG. 5 illustrates a layout example of the ultraviolet light sources 200 of FIG. 4 according to the present exemplary embodiment. The ultraviolet light source 200a is included in the scanner unit 13. In order to optimize the angle between the operation unit 12 and the ultraviolet light source 200a, the ultraviolet light source 200a is situated at a high position in the scanner unit 13. In order to irradiate the operation unit 12 with irradiation light from the ultraviolet light source 200a, the ultraviolet light source 200a is obliquely disposed. The ultraviolet light source 200b is included in the scanner unit 13. In order to irradiate a handle for opening the platen or the automatic conveyance device of the scanner unit 13 in using the scanner unit 13 at a shortest distance, the ultraviolet light source 200b is situated at a lower position of the handle of the scanner unit 13.

The ultraviolet light source 200c is at a depressed part where the power switch 250 is situated. For a seesaw switch SW as the power switch 250, the ultraviolet light source 200c is provided to both the upper part and the lower part of the depressed part such that the surface of the power switch 250 in ON or OFF state is irradiated at a shortest distance. The ultraviolet light source 200c can be provided to both the right side and the left side depending on the orientation of the power switch 250. For a tactile switch SW as the power switch 250, the ultraviolet light source 200c is provided on the upper, lower, right, or left side of the depressed part such that the overall power switch 250 is irradiated.

Each of the ultraviolet light sources 200d is situated at the corresponding one of sheet feeding cassettes 15. Each ultraviolet light source 200d is situated at the back part of a handle of the corresponding one of the sheet feeding cassettes 15 such that the handle used in placing sheets in the corresponding sheet feeding cassette 15 is irradiated at a shortest distance.

A lifetime management control method of adjusting the light quantity with the above-described configuration to guarantee sterilization performance while considering user convenience will be described below.

A lifetime management control method will be described with respect to reducing a user's waiting time during sterilization processing to ensure user convenience and the product lifetime of each ultraviolet light source 200 by adjusting the light quantity of the ultraviolet light source 200 according to the present exemplary embodiment. The control that will be described is performed by loading a program stored in the ROM 206 or the storage 207 of the controller 11 of the image forming apparatus 100 in FIG. 2 to the RAM 205 and thereafter running the loaded program by the CPU 202.

First, details of the lifetime management of the ultraviolet light sources 200 in use will be described. FIGS. 6A and 6B illustrate management data that manages product lifetime information and product usage information. Specifically, for product lifetime management, the image forming apparatus 100 stores information such as setting values, and calculates and stores a deterioration integrated point (613) based on a set light quantity and a measured irradiation time. The setting values and the management data will be described below with reference to FIG. 6A. The above-described data is stored in the ROM 206 or the storage 207 of the controller 11. In the present exemplary embodiment, each ultraviolet light source 200 uses a light emitting diode (LED) with a lifetime of 30,000 hours (light quantity: 70%) as a reference time for replacement as a result of continuous use with irradiation output at its reference light quantity.

For example, 30,000 hours is converted into 108,000,000 seconds, and a numerical value of 108,000,000 is a lifetime end point 601. The image forming apparatus 100 stores a lifetime deterioration rate with a set high output light quantity and a lifetime deterioration rate with a set low output light quantity, for both of which the corresponding irradiation time is added up. When an integrated illuminance, the product of an illuminance and its irradiation time, is satisfied as the sterilization condition, sterilization is completed.

A doubled light source output halves the irradiation time of sterilization. As a result, an increase of an irradiation output via setting a light quantity reduces a user's waiting time during the ultraviolet irradiation in sterilization, improving convenience. However, an increase of a light quantity leads to a significant decrease in the product lifetime of the ultraviolet light source. Consequently, there are demands for a configuration that uses an ultraviolet light source at a light quantity during an irradiation time based on the way a user uses while reducing the user's waiting time for sterilization, the configuration of which meets both the product lifetime of the ultraviolet light source and user's convenience.

The light quantity and irradiation time setting will be described below with reference to FIGS. 7A to 7G illustrating examples of screens on the operation unit 12. A lifetime deterioration rate α 604 with a reference light quantity set is set to one. A lifetime deterioration development level is expressed as the product of an irradiation time and the lifetime deterioration rate α 604 and is one-fold. In this case, the time for sterilization (reference light quantity setting sterilization time 607) is approximately 16 seconds.

According to the present exemplary embodiment, since each ultraviolet light source 200 has a sufficient product lifetime for the setting value, a deterioration rate β 605 is set to two, which makes the low output light quantity setting to produce twice the irradiation output at the reference. In this case, the time for sterilization (low output light quantity setting sterilization time 608) is reduced to 8 seconds, which is half the time at the reference light quantity.

Next, a deterioration rate γ 606 is set to four, which makes the high output light quantity setting to produce four times the irradiation output at the reference. In this case, the time for sterilization (high output light quantity setting sterilization time 609) is 4 seconds, which is one-fourth the time at the reference light quantity. The main SOC 201 accesses each light quantity control unit 212 and sets the light quantity settings. The main SOC 201 instructs each output control unit 213 to turn on the corresponding ultraviolet light source 200, counts the time that passes, and turns off the corresponding ultraviolet light source 200 if the counted time reaches a predetermined time. The time is counted using a real time clock IC (not illustrated) or a software counter (not illustrated) of the controller 11. The deterioration integrated point 613 is calculated based on the above-described setting values for the lifetime management.

While control is performed using the two settings that are the high output setting and the low output setting according to the present exemplary embodiment, any possible configurations with more settings (e.g., five levels) and divided cases can be used.

Settings for different uses will be described with reference to FIGS. 7A to 7G illustrating examples of screens on the operation unit 12. FIG. 6B illustrates a list of management data with the deterioration integrated point 613 calculated for each ultraviolet light source 200. An integrated illuminance condition entails a long low output irradiation time in sterilization, but at higher outputs, the irradiation time decreases. A configuration is used that changes settings depending on the use to use each ultraviolet light source 200 while managing the product lifetime of the ultraviolet light source 200.

For example, control modes "prioritize lifetime 701", "prioritize speed 702", and "balance 703" are settable as illustrated in FIG. 7A. According to the present exemplary embodiment, control is performed based on each control mode. With the prioritize lifetime 701 selected, the setting for the irradiation output from an ultraviolet light source 200 is set to the low output light quantity setting by the light quantity control unit 212. A lifetime deterioration rate for use in calculating the deterioration integrated point 613 is the lifetime deterioration rate β 605. That increases the sterilization time, but the concern about the product lifetime decreases. The prioritize lifetime 701 setting is suitable for, for example, the ultraviolet light source 200c situated at the power switch 250, which is typically touched once or twice a day, and the ultraviolet light source 200d situated at the handle for opening/closing the sheet feeding cassette 15, which is less frequently touched.

According to the present exemplary embodiment, a management data column 623 for the ultraviolet light source 200c and a management data column 624 for the ultraviolet light source 200d in the table in FIG. 6B are for the prioritize lifetime 701 setting, and a low output integrated time 611 alone is recorded. A deterioration state of the ultraviolet light source 200c will be described below as an example with reference to the column 623 in FIG. 6B. The integrated irradiation time of the ultraviolet light source 200c configured to perform sterilization near the power switch 250 is 11,680 seconds.

A deterioration development level is calculated using the lifetime deterioration rate β 605=2, so that the deterioration integrated point 613 of the ultraviolet light source 200c is 11,680×2=23,360.

Next, with the prioritize speed 702 set, the setting for the irradiation output from an ultraviolet light source 200 is set to the high output light quantity setting by the light quantity control unit 212. A lifetime deterioration rate for use in calculating the deterioration integrated point 613 is the lifetime deterioration rate γ 606. That reduces the sterilization time, and thus the user's waiting time. However, as that accelerates the lifetime deterioration, parts of the ultraviolet light source 200 can be subject to replacement. The prioritize speed 702 setting is a mode set by the user with priority given to convenience and is suitable as a setting for the ultraviolet light sources 200a and 200b situated at the operation unit 12 and the scanner unit 13, which are typically frequently touched by a large number of unspecified users.

According to the present exemplary embodiment, a management data column 621 for the ultraviolet light source 200a in the table in FIG. 6B is for the prioritize speed 702 setting, and a high output integrated time 612 alone is recorded. A deterioration state of the ultraviolet light source 200a will be described below as an example with reference to the column 621 in FIG. 6B. The integrated irradiation time of the ultraviolet light source 200a configured to perform sterilization near the operation unit 12 is 2,702,500 seconds. A deterioration development level is calculated using the lifetime deterioration rate γ 606=4, so that the deterioration integrated point 613 of the ultraviolet light source 200a is 25,650,000×4=102,600,000. The calculated deterioration integrated point 613 typically reaches the numerical value of a lifetime warning point 602 in the table in FIG. 6A.

According to the present exemplary embodiment, a numerical value that is 95% the product lifetime is used as a setting value of the lifetime warning point 602. FIG. 7B illustrates an example of a screen notification on the LCD 351 of the operation unit 12 to the user with the deterioration integrated point 613 reaching the lifetime warning point 602. The notification is a warning level because the deterioration integrated point 613 has not reached 100% at this time. If the deterioration integrated point 613 exceeds the lifetime end point 601 corresponding to 100%, at which the sterilization performance is no longer ensured, a screen notification prompting the user to replace the parts is displayed on the LCD 351 as in the example illustrated in FIG. 7C.

Next, with the balance 703 set, the setting for the irradiation output from an ultraviolet light source 200 is set to change the output light quantity based on the state by the light quantity control unit 212. This is a setting mode considering the product lifetime as well as user convenience. In the setting mode, the sterilization is normally performed at low output over a long period of time, but if it is determined that there is a next user waiting to use the image forming apparatus 100, the setting is changed to the high output setting to perform sterilization in a short period of time so that the user will not have to wait. Details of the processing will be described below with reference to the flowcharts illustrated in FIGS. 8A, 8B1, and 8B2. The balance 703 setting is suitable as a setting for the ultraviolet light sources 200a and 200b situated at the operation unit 12 and the scanner unit 13, which are typically frequently touched by a large number of unspecified users, as with the case where the prioritize speed 702 is set.

According to the present exemplary embodiment, a management data column 622 for the ultraviolet light source 200b in the table in FIG. 6B is for the balance 703 setting, and since the output light quantity is changed based on the state, the integrated time 611 for the low output setting and the integrated time 612 for the high output setting based on the setting are each recorded. A deterioration state of the ultraviolet light source 200b will be described below as an example with reference to the column 622 in FIG. 6B. The integrated irradiation times of the ultraviolet light source 200b configured to perform sterilization near the scanner unit 13 are 48,540,000 seconds for the low output and 30,100 seconds for the high output, respectively. A deterioration development level is calculated using the lifetime deterioration rate β 605=2 and the lifetime deterioration rate γ 606=4, so that the deterioration integrated point 613 of the ultraviolet light source 200b is 48,540,000×2+30,100×4=97, 320,800. The calculated deterioration integrated point 613 typically exceeds a lifetime caution point 603 in the table in FIG. 6A.

According to the present exemplary embodiment, a numerical value that is 90% the product lifetime is used as a setting value of the lifetime caution point 603. FIG. 7D illustrates an example of a screen notification on the LCD 351 of the operation unit 12 to the user with the deterioration integrated point 613 reaching the lifetime caution point 603. The notification is a 90% caution level at this time, so that the notification just prompts the user to prepare replacement parts. The data on the product lifetime is managed as described above.

FIG. 8A is a flowchart illustrating a user operation detection management process according to the present exemplary embodiment. FIGS. 8B1 and B2 is a flowchart illustrating a lifetime management control process according to the present exemplary embodiment for ensuring sterilization performance while considering user convenience by adjusting the light quantity of the ultraviolet light sources 200. The process procedures are applied to all the ultraviolet light sources 200a, 200b, 200c, and 200d at the operation unit 12, the scanner unit 13, the power switch 250, and the sheet feeding cassette 15. The ultraviolet light sources 200a, 200b, 200c, and 200d will be referred to as "the ultraviolet light source 200". The control according to the present exemplary embodiment is carried out by loading a program stored in the ROM 206 or the storage 207 of the controller 11 of the image forming apparatus 100 in FIG. 2 to the RAM 205 and thereafter running the loaded program by the CPU 202.

Turning to FIG. 8A, the illustrated procedure is initiated in response to the start of an operation by the user. In step S800, the main SOC 201 detects whether a user operation is performed at a part where the ultraviolet light source 200 is situated, and an operation detection flag is set for the part operated by the user.

The operation unit 12, the scanner unit 13, the power switch 250, and the sheet feeding cassette 15 have an operation detection system, and each functional unit can perform detection as described below. The operation unit 12 detects an operation if the touch panel 352, the numeric keypad 353, or the card reader 354 is operated, and an operation detection flag is set. The scanner unit 13 has a mechanism for opening and closing, and detects an operation with sensors if the mechanism for opening and closing is operated by the user, and an operation detection flag is set. The power switch 250 is touched by the user to turn the power on, and when the power switch 250 is turned on, an operation detection flag is set. The sheet feeding cassette 15 has a mechanism for opening and closing similarly to the scanner unit 13, and if a user operation is performed, the sheet feeding cassette 15 detects the user operation using sensors, and an operation detection flag is set. The operation detection flags are stored as state data in the RAM 205. An operation detection flag can be set if an opening/closing operation on a sheet feeding tray is detected. Configurations are not limited to the above-described configurations.

In step S801, if the user operation has ended (YES in step S801), the procedure ends. If the user operation has not yet ended, (NO in step S801), the processing returns to step S800.

The phrase "the user starts an operation" refers to receiving a user operation to cause the image forming apparatus 100 in a sleep state to transition to a standby state, the receiving of a user operation when the image forming apparatus 100 is turned on, or the receiving of a user operation after the image forming apparatus 100 is turned on. The phrase "the user starts an operation" with a user authentication function provided can refer to a case where an integrated circuit (IC) is detected or a case where an operation for opening a user ID and password input screen for user authentication is received. A user detection function, such as a human detecting sensor, detecting a user can be regarded as a user operation start. The above examples are not seen to be limiting, and any user operation that enables practice of the present embodiment is applicable.

FIGS. 8B1 and 8B2 will now be described. The procedure illustrated in FIGS. 8B1 and 8B2 is initiated in response to the end of the user operation.

In step S802, the main SOC 201 checks whether an operation detection flag is set.

If an operation is detected in step S801, a detection flag is set (YES in step S802), and the processing proceeds to step S803. If a detection flag is not set (NO in step S802), i.e., no touch operations have been performed, the ultraviolet light source 200 does not perform sterilization, and the procedure ends.

In step S803, the main SOC 201 proceeds to a process with an operation detection flag set.

Figure 7F:
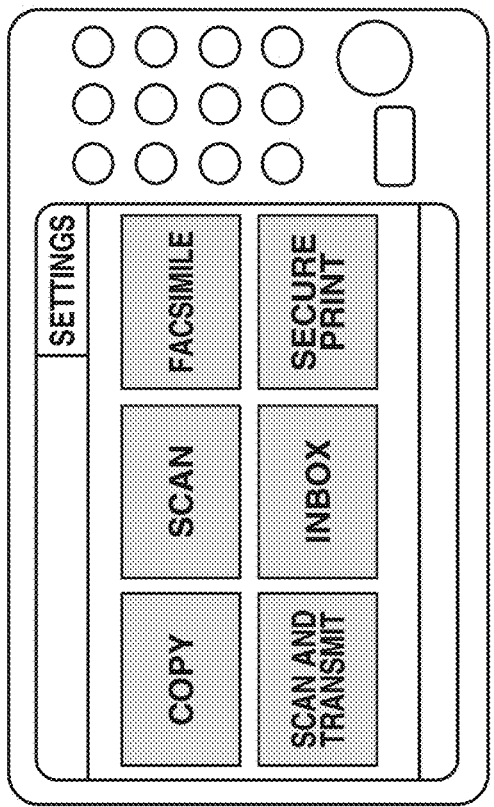
Figure 7E:
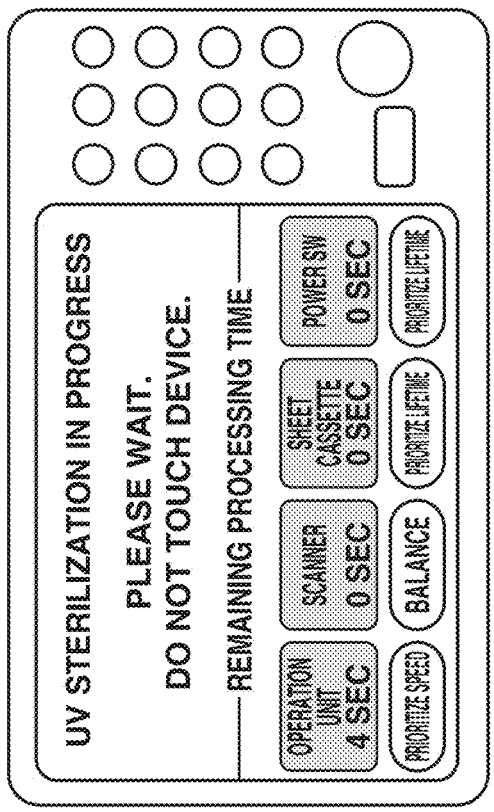

If a part to be sterilized is touched by the user, the UI controller 355 is instructed to change an image display on the LCD 351 of the operation unit 12 to a screen, for example, as illustrated in FIG. 7E. In FIG. 7E, a message is displayed to prompt the user to wait without touching the device until the UV sterilization ends. The main SOC 201 can instruct the UI controller 355 to invalidate input signals from the touch panel 352 and the numeric keypad 353 in order to prevent a touch by the user until the sterilization processing ends.

In step S804, the main SOC 201 checks an irradiation pattern setting for the ultraviolet light source 200. This is the setting "the prioritize lifetime 701", "prioritize speed 702", or "balance 703" in FIG. 7A. An irradiation pattern setting can be set for each of the ultraviolet light sources 200a, 200b, 200c, and 200d. The irradiation pattern setting is preset by the user or a reference setting is set, and the set setting is stored in the ROM 206 or the storage 207. If the setting is "the prioritize lifetime 701" ("PRIORITIZE LIFETIME" in step S804), the processing proceeds to step S805. If the setting is "prioritize speed 702" ("PRIORITIZE SPEED" in step S804), the processing proceeds to step S815. If the setting is "balance 703" ("BALANCE" in step S804), the processing proceeds to step S818.

First, a process for the setting of "the prioritize lifetime 701" will be described. In step S805, the main SOC 201 transmits an instruction to change to the low output light quantity setting to the light quantity control unit 212 and transmits an ON instruction to the output control unit 213 to start irradiation with the ultraviolet light source 200. A remaining time before the end of the sterilization by the irradiation with the ultraviolet light source 200 is displayed as a screen, as illustrated in the example in FIG. 7E.

In step S806, after a predetermined time passes, the main SOC 201 transmits an OFF instruction to the output control unit 213 to stop the irradiation with the ultraviolet light source 200. According to the present exemplary embodiment, since the sterilization by the irradiation with the ultraviolet light source 200 at the low output light quantity setting takes 8 seconds, the irradiation is stopped in 8 seconds in step S806.

In step S807, the main SOC 201 integrates the time of the irradiation with the ultraviolet light source 200 in steps S805 and S806 as the low output irradiation time and stores the integrated irradiation time. The main SOC 201 calculates the deterioration integrated point 613 using the stored integrated time and updates the deterioration integrated point 613 with the calculated deterioration integrated point 613. Details of the calculation have been described above with reference to FIGS. 6A and 6B, and redundant descriptions thereof will be omitted herein.

In step S808, the main SOC 201 deletes the operation detection flag corresponding to the complete sterilization. In step S819, the main SOC 201 checks whether another operation detection flag is set. If another operation detection flag is set (YES in step S819), the processing returns to step S803. If another operation detection flag is not set (NO in step S819), the processing proceeds to step S809. Step S819 can be performed after below-described steps S811, S813, S814, and S809 (NO).

Next, in step S809, the main SOC 201 determines whether the calculated deterioration integrated point 613 has reached one of the set lifetime threshold values. The lifetime threshold values are numerical values of the lifetime end point 601, the lifetime warning point 602, and the lifetime caution point 603 in the table in FIG. 6A. If the deterioration integrated point 613 has not reached any of the set lifetime threshold values (NO in step S809), the sterilization processing ends. If the deterioration integrated point 613 has reached one of the set lifetime threshold values (YES in step S809), the processing proceeds to step S810.

In step S810, if the deterioration integrated point 613 has reached the set lifetime end point 601 (YES in step S810), the processing proceeds to step S811 to prompt the user regarding the product lifetime to replace the ultraviolet light source 200. In step S811, a screen notification to the user is displayed on the LCD 351 of the operation unit 12 as illustrated in FIG. 7C. If "GO TO REPLACEMENT" in FIG. 7C is selected, the processing proceeds to FIG. 9 described below.

In step S810, if the deterioration integrated point 613 has not reached the set lifetime end point 601 (NO in step S810), the processing proceeds to step S812.

In step S812, if the deterioration integrated point 613 has reached the set lifetime warning point 602 (YES in step S812), the processing proceeds to step S813 to display a warning message to the user. Specifically, in step S813, a screen notification to the user is displayed on the LCD 351 of the operation unit 12 as illustrated in FIG. 7B. If "GO TO REPLACEMENT" is selected in FIG. 7B, the processing proceeds to FIG. 9 described below. If the deterioration integrated point 613 has not reached the set lifetime warning point 602 (NO in step S812), as the deterioration integrated point 613 has reached the lifetime caution point 603, the user is prompted to prepare replacement parts for the ultraviolet light source 200. Specifically, in step S814, a screen notification to the user is displayed on the LCD 351 of the operation unit 12 as illustrated in FIG. 7D.

Following steps S811, S813, and S814, the processing in the flowchart of FIGS. 8B1 and 8B2 ends.

The case of the setting of "prioritize speed 702" ("PRIORITIZE SPEED" in step S804) will now be described. In step S815, the main SOC 201 transmits an instruction to change to the high output light quantity setting to the light quantity control unit 212 and transmits an ON instruction to the output control unit 213 to start irradiation with the ultraviolet light source 200. Similarly, a remaining time before the end of the sterilization by the irradiation with the ultraviolet light source 200 is displayed as illustrated in the example of FIG. 7E.

In step S816, after a predetermined time passes, the main SOC 201 transmits an OFF instruction to the output control unit 213 to stop the irradiation with the ultraviolet light source 200. According to the present exemplary embodiment, the sterilization by the irradiation with the ultraviolet light source 200 at the low output light quantity setting takes 4 seconds, and the irradiation is stopped in 4 seconds in step S816.

In step S817, the main SOC 201 integrates the time of the irradiation with the ultraviolet light source 200 in steps S815 and S816 as the high output irradiation time and stores the integrated irradiation time. The main SOC 201 calculates the deterioration integrated point 613 using the stored integrated time and updates the deterioration integrated point 613 with the calculated deterioration integrated point 613. Details of the calculation have been described above with reference to FIGS. 6A and 6B, and redundant descriptions thereof will be omitted herein. Step S808 and the subsequent steps are similar to those described, and redundant descriptions thereof will be omitted herein.

Next, the case of the setting of "balance 703" ("BALANCE" in step S804) will be described. The procedure is based on the assumption that another user is waiting to use the image forming apparatus 100, and that the irradiation is performed at the high output light quantity and completes in a short time to reduce the user's waiting time. If it is determined that there no additional users waiting, sterilization is controlled to be performed at the low output light quantity.

In step S818, the main SOC 201 checks whether a job is stored in the job queue to determine whether a job for a next user is waiting if the use by the previous user is complete and the sterilization is to be performed. If a job is stored in the job queue (YES in step S818), in order to complete the sterilization in a short time, the processing proceeds to step S815, which is the same process procedure as the prioritize speed 702 setting. If there is no user waiting (NO in step S818), which means no need to complete the sterilization in a short time, the processing proceeds to step S805, which is the same process procedure as the prioritize lifetime 701 setting. The subsequent process runs as described, and redundant descriptions thereof will be omitted herein.

In the foregoing process procedures, sterilization is performed by ultraviolet irradiation at the high output light quantity in a short time to prioritize speed, and by ultraviolet irradiation at the low output light quantity to prioritize product lifetime. In addition, sterilization is performed in a balanced use of the ultraviolet irradiation at the high and low output light quantities. Lifetime data corresponding to the operations is managed, which enables operations without deterioration in sterilization performance. The above-described configuration enables use of a method of controlling operations for ensuring sterilization performance by managing the product lifetime while considering user convenience by adjusting the light quantity of the ultraviolet light source 200. A setting for not using the ultraviolet light source 200 can be provided in FIG. 7A. In this case, step S804 has a branch of "use no ultraviolet light sources" which results in the processing ending.

The phrase "the user ends the operation" refers to a change of the image forming apparatus 100 to a sleep state after receiving no user operations for a predetermined time, a change of the image forming apparatus 100 to the sleep state at the press of a power saving key, and a process of starting shutting down the image forming apparatus 100. The phrase "the user ends the operation" with the user authentication function provided can refer to logout processing by the user. With the user detection function, such as a human detecting sensor provided, no longer detecting a user can be regarded as the end of a user operation.

After the flowchart in FIGS. 8B1 and 8B2 ends, the main SOC 201 changes the state of the LCD 351 of the operation unit 12. The state can be changed based on the details of "the user ends the operation". For example, the screen display is turned off if the state is changed to the sleep state, the shutdown processing is performed, or the human detecting sensor no longer detects the user. In another example, the screen returns to a home screen if the user performs logout processing or the human detecting sensor no longer detects the user.

Next, a process procedure of replacing the ultraviolet light source 200 that has reached the end of the product lifetime in the process procedure in FIGS. 8B1 and 8B2 and clearing the management data will be described with reference to FIG. 9. According to the present exemplary embodiment, the ultraviolet light source 200 is a light device including a simple light source circuit. The control according to the present exemplary embodiment is similarly carried out by loading a program stored in the ROM 206 or the storage 207 of the controller 11 of the image forming apparatus 100 in FIG. 2 to the RAM 205 and thereafter running the loaded program by the CPU 202.

Figure 7G:
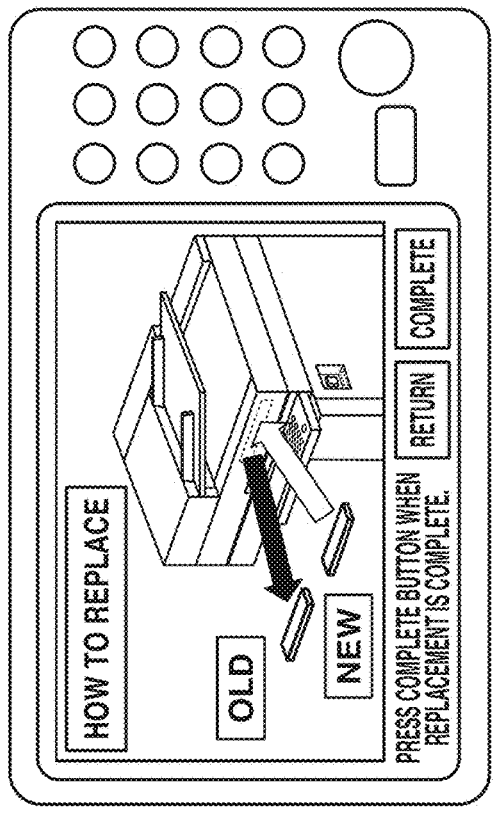

In step S901, the main SOC 201 changes to a mode for replacing the ultraviolet light source 200. The ultraviolet light source 200 is a replaceable part connected to the removable connector 214. The ultraviolet light source 200 is connected via electric circuitry. Thus, in replacing the ultraviolet light source 200, the main SOC 201 controls the output control unit 213 to change the circuit state to enable physical connector separation. When it is determined that the lifetime does not ensure the sterilization performance in the process according to the present exemplary embodiment, the image forming apparatus 100 shifts to the mode for replacing the ultraviolet light source 200 in response to the selection of "GO TO REPLACEMENT" in FIG. 7B or 7C. During the replacement, a procedure screen, as illustrated in the example in FIG. 7G, is displayed on the LCD 351 of the operation unit 12.

In step S902, the main SOC 201 determines whether the replacement of the ultraviolet light source 200 is complete and a complete instruction is received from the user. The instruction is issued in response to selection of a COMPLETE button on a screen as an example in FIG. 7G. The notification from the UI controller 355 to the main SOC 201 enables the determination that the replacement is complete. If a replacement complete instruction is received (YES in step S902), the processing proceeds to step S904. If a replacement complete instruction is not received (NO in step S902), the processing proceeds to step S903.

In step S903, if the mode for replacing the ultraviolet light source 200 has been started but a cancel instruction is issued due to lack of a replacement ultraviolet light source 200 (YES in step S903), the procedure ends. If no cancel instructions are received (NO in step S903), a complete instruction from the user is awaited.

In step S904, if a replacement complete instruction from the user is received, the irradiation integrated times (611, 612) and the deterioration integrated point (613) for lifetime management are cleared. For example, if the ultraviolet light source 200a near the operation unit 12 is replaced, the data in the column 621 is all cleared to zero. Data before the replacement can be retained as previous history data in another area of the ROM 206 or the storage 207 of the controller 11, and new management data can start with zero. The main SOC 201 can acquire model number information about the replaced ultraviolet light source and can set the lifetime end point 601, the lifetime warning point 602, and the lifetime caution point 603 for the replaced ultraviolet light source based on the acquired model number information.

A process procedure of replacing the ultraviolet light source 200 has been described above. To replace the ultraviolet light source 200 with the power off, the user can manually clear the counter. The ultraviolet light source 200 can include a non-volatile memory such as the ROM 206 instead of the light device including simple light source circuitry to distinguish whether the ultraviolet light source 200 is a new product. In this case, a process similar to step S904 can be performed by transmitting a notification from the ultraviolet light source control unit 220 to the main SOC 201. As described above, any configurations configured to detect replacement enable the processing to proceed to the clearing of the management data. Thus, any possible configurations that would enable practice of the present exemplary embodiments can be used.

Other Exemplary Embodiments

Embodiment(s) can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While exemplary embodiments have been described, these embodiments are not seen to be limiting. The scope of the following claims is to be accorded the broadest interpretation so as to encompass all such modifications and equivalent structures and functions.

This application claims the benefit of Japanese Patent Application No. 2021-082585, filed May 14, 2021, which is hereby incorporated by reference herein in its entirety.

What is claimed is:

1. An image forming apparatus comprising:
   an ultraviolet light source configured to irradiate an operation unit including a touch panel of the image forming apparatus for sterilization; and
   a controller configured to:
      display a setting screen for setting a control mode of the ultraviolet light source;
      receive, from a user, a selection of the control mode from a first control mode, a second control mode and a third control mode on the setting screen;
      control the ultraviolet light source to perform irradiation in the first control mode in which a first irradiation time and a first irradiation output are used in a case where the first control mode is selected;
      control the ultraviolet light source to perform irradiation in the second control mode in which a second irradiation time shorter than the first irradiation time and a second irradiation output higher than the first irradiation output are used in a case where the second control mode is selected;
      control the ultraviolet light source to perform irradiation in the first control mode in a case where the third control mode is selected and where a job of a next user who subsequently uses the image forming apparatus is not in a job queue;
      control the ultraviolet light source to perform irradiation in the second control mode in a case where the third control mode is selected and where the job of the next user is in the job queue.

2. The image forming apparatus according to claim 1, further comprising a plurality of ultraviolet light sources, wherein the controller receives a selection of a control mode for each of the plurality of ultraviolet light sources.

3. The image forming apparatus according to claim 1, further comprising a storage configured to store lifetime information corresponding to a product lifetime of the ultraviolet light source and usage information corresponding to an irradiation time and an irradiation output of the ultraviolet light source.

4. The image forming apparatus according to claim 1, wherein the storage stores a result of calculating a product of the first irradiation time and a first deterioration rate corresponding to the first irradiation output and a result of calculating a product of the second irradiation time and a second deterioration rate corresponding to the second irradiation output.

5. The image forming apparatus according to claim 4, wherein the second deterioration rate is greater than the first deterioration rate.

6. The image forming apparatus according to claim 3, wherein the lifetime information is a result of calculating a product of a deterioration rate in a case where the ultraviolet light source is used at a predetermined irradiation output and a time to a sufficient product lifetime of the ultraviolet light source in a case where the ultraviolet light source is continuously used at the predetermined irradiation output.

7. The image forming apparatus according to claim 3, wherein the controller provides a first notification to prompt the user to prepare a replacement part for the ultraviolet light source in a case where the usage information exceeds a first threshold value with respect to the lifetime information, and provides a second notification to prompt the user to replace the ultraviolet light source in a case where the usage information exceeds a second threshold value greater than the first threshold value.

8. The image forming apparatus according to claim 7, wherein the controller provides a third notification to notify the user that the product lifetime of the ultraviolet light source is close to an end of life value in a case where the usage information exceeds a third threshold value with respect to the lifetime information, and wherein the third threshold value is greater than the first threshold value and less than the second threshold value.

9. The image forming apparatus according to claim 3, further comprising a sensor configured to detect a user operating on a part of the image forming apparatus,
   wherein the storage stores information associated with the part operated on by the user, and
   wherein the controller controls the ultraviolet light source to irradiate the part associated with the stored information.

10. The image forming apparatus according to claim 9, further comprising a scanner device including a platen or an automatic conveyance device,
    wherein the part of the image forming apparatus operated on includes a part for opening and closing the platen or the automatic conveyance device.

11. The image forming apparatus according to claim 9, further comprising a printer device including at least one sheet feeding cassette,
    wherein the part of the image forming apparatus operated on includes a part for opening and closing the sheet feeding cassette.

12. A method of controlling an image forming apparatus including an ultraviolet light source configured to irradiate an operation unit including a touch panel of the image forming apparatus for sterilization, the method comprising:
    displaying a setting screen for setting a control mode of the ultraviolet light source;
    receiving, from a user, a selection of the control mode from a first control mode, a second control mode and a third control mode on the setting screen;

controlling the ultraviolet light source to perform irradiation in the first control mode that is a first irradiation time and a first irradiation output in a case where the first control mode is selected;

controlling the ultraviolet light source to perform irradiation in the second control mode that is a second irradiation time shorter than the first irradiation time and a second irradiation output higher than the first irradiation output in a case where the second control mode is selected;

controlling the ultraviolet light source to perform irradiation in the first control mode in a case where the third control mode is selected and where a job of a next user who subsequently uses the image forming apparatus is not in a job queue; and controlling the ultraviolet light source to perform irradiation in the second control mode in a case where the third control mode is selected and where the job of the next user is in the job queue.

13. The image forming apparatus according to claim 3, wherein the storage stores the first irradiation time and the second irradiation time separately as the irradiation time of the ultraviolet light source.

\* \* \* \* \*